United States Patent [19]
Healy et al.

[11] Patent Number: 5,214,157
[45] Date of Patent: May 25, 1993

[54] PROCESS FOR THE DISPOSAL OF PHTHALIC ANHYDRIDE DECOMPOSER VAPORS

[75] Inventors: Francis J. Healy, Florham Park, N.J.; Herbert P. Dengler, Baton Rouge, La.

[73] Assignee: Exxon Chemical Patents Inc., Linden, N.J.

[21] Appl. No.: 696,903

[22] Filed: May 7, 1991

[51] Int. Cl.$^5$ .................................. C07D 307/89
[52] U.S. Cl. ........................... 549/250; 549/247
[58] Field of Search ......................... 549/247, 250

[56] References Cited

U.S. PATENT DOCUMENTS

| | | | |
|---|---|---|---|
| 3,178,452 | 4/1965 | Smith et al. | 260/346.4 |
| 3,303,203 | 2/1967 | Melnstein | 260/346.7 |
| 3,397,121 | 8/1968 | Fitzgerald | 203/35 |
| 3,507,886 | 4/1970 | Suter et al. | 260/346.7 |
| 3,650,906 | 3/1972 | Gehrken et al. | 203/89 |
| 3,655,521 | 4/1972 | Gehrken et al. | 203/28 |
| 3,725,211 | 4/1973 | Gehrken et al. | 203/74 |
| 3,886,050 | 5/1975 | Deutner et al. | 549/250 |
| 4,215,055 | 7/1980 | Palmer et al. | 549/250 |
| 4,233,264 | 11/1980 | Maude et al. | 549/247 |
| 4,252,772 | 2/1981 | Way | 549/250 |
| 4,285,871 | 8/1981 | Keunecke et al. | 549/250 |
| 4,430,163 | 2/1984 | Alberts et al. | 549/250 |
| 4,906,760 | 3/1990 | Mueller et al. | 549/250 |

FOREIGN PATENT DOCUMENTS

| | | | |
|---|---|---|---|
| 3339392 | 5/1985 | Fed. Rep. of Germany | 549/250 |
| 2114984 | 5/1987 | Japan | 549/250 |

*Primary Examiner*—Cecilia Tsang

[57] ABSTRACT

A system for producing phthalic anhydride by vapor phase oxidation of orthoxylene, naphthalene or the like which comprises an oxidation section, and a finishing section comprising: a means for decomposing crude phthalic anhydride liquid such that water, various other by-products and small amounts of phthalic anhydride are removed from the crude phthalic anhydride liquid as decomposer vapor; a means for venting decomposer vapor directly to a top portion of a first fractionation column; the first fractionation column being capable of distilling crude phthalic anhydride liquid received from the decomposer means for the purpose of removing light ends therefrom and which is also capable of recovering phthalic anhydride contained within vapors being vented therefrom; and a second fractionation column capable of distilling the crude phthalic anhydride liquid from the first fractionation column and removing tailings therefrom to produce substantially pure phthalic anhydride; whereby phthalic anhydride is recovered from the decomposer vapor and whereby use of a decomposer condenser and associated jet ejectors or vacuum pumps are avoided.

10 Claims, 3 Drawing Sheets

PROCESS FOR THE DISPOSAL OF PHTHALIC ANHYDRIDE DECOMPOSER VAPORS

The present invention relates primarily to a system and process for producing substantially pure phthalic anhydride from crude phthalic anhydride. Crude phthalic anhydride is typically produced via vapor phase oxidation of orthoxylene, naphthalene, and/or any other material capable of being catalytically converted to phthalic anhydride. For example, production of phthalic anhydride from air and orthoxylene normally occurs in two stages, i.e., an oxidation section and a finishing section. The oxidation section produces a crude phthalic anhydride liquid and the finishing section produces a substantially pure phthalic anhydride product. The present invention is directed to an improvement in the finishing section which comprises a means for venting decomposer vapor directly to a top portion of a first fractionation column; whereby phthalic anhydride is recovered from the decomposer vapor and whereby use of a decomposer condenser and associated jet ejectors or vacuum pumps are avoided.

BACKGROUND OF THE INVENTION

Phthalic anhydride is an important commercial chemical useful in the manufacture of dyes and resins. Phthalic anhydride is also an intermediate compound used principally in the manufacture of plasticizers, polyesters and alkyd resins. The color properties of this material are particularly important, especially when the phthalic anhydride is used in the production of alkyd resins, these latter materials being used as coatings in the finishes of automobiles, refrigerators, etc. The plasticizers are of two types: diesters of a monohydric alcohol, e.g., dibutyl phthalate, and mixed esters of two monohydride alcohols.

The fastest-growing use of phthalic anhydride is in the production of unsaturated polyester resins, which are the products of polycondensation reactions between mole equivalents of certain dicarboxylic acids and glycols. Resins based on phthalic anhydride are used widely in the construction, marine, and synthetic-marble industries. In most cases, the resins contain mineral or glass fibers which provide the required structural strength.

Phthalic anhydride is typically produced from raw materials such as orthoxylene (o-xylene), petroleum naphthalene, and coal-tar naphthalene. The price of these raw materials and, as a direct result, the price of phthalic anhydride have fluctuated greatly depending upon supply and demand. Because the cost of the raw materials are a major factor in the price of phthalic anhydride it is of great importance that any system used to produce phthalic anhydride capture as much of the resultant product as possible.

Phthalic anhydride can be successfully produced from any of a number of processes, i.e., (1) air oxidation of o-xylene in fixed-bed reactors, (2) air oxidation of petroleum or coal tar naphthalene in fixed-bed reactors, (3) fluid bed oxidation of o-xylene, (4) fluid bed oxidation of petroleum or coal tar naphthalene, and (5) liquid phase oxidation of o-xylene or naphthalene.

The general process scheme for the various vapor phase routes is to mix the hydrocarbon feed (in the vapor form) with compressed air and to feed the mixture to fixed-bed reactors which contain tubes packed with catalysts, e.g., vanadium oxide and titanium dioxide coated on an inert, nonporous carrier. When fluid bed reactors are used, the hydrocarbon feed in liquid form is injected directly into the fluidized bed so that the air and the hydrocarbon are mixed in the reactor. The reactors are equipped with means for removing the heat of the oxidation reactions that occur. The heat that is removed is used to generate steam.

In fluid bed reactors, provisions are made to cool the reaction mixture immediately after it leaves the reaction zone. This operation, called "quenching," is done to stop the reactions and to prevent "after-burning."

After the product stream exits either the fixed-bed or fluid bed reactors, it is cooled to cause the phthalic anhydride to condense. This allows separation of the phthalic anhydride from the gas stream. In fixed-bed systems, the phthalic anhydride is typically condensed as a solid. However, a two-stage condensation system can be used to first condense a portion of the phthalic anhydride as a liquid and then to condense the remainder as a solid.

Switch condensers that operate alternately on a cooling cycle and a heating cycle are used to collect the phthalic anhydride as a solid. The solid is then melted for removal from the condensers.

The crude phthalic anhydride is usually heat-treated in a decomposer, but in some cases chemical treatment is also used. The heat treatment is carried out by holding the molten crude at an elevated temperature [approximately 500° F.] for a period of 12-36 hours and usually under a small vacuum. The purpose of the heat treatment is to dehydrate any phthalic acid in the crude to phthalic anhydride, to boil off materials such as water, and to form either condensation or volatile products with the other impurities so that the subsequent product purification by distillation is simplified.

After distillation, the pure molten product may be solidified, flaked, bagged, and stored in a warehouse. Alternatively, the molten product may be pumped into large storage tanks and then into tank cars for shipment.

One conventional system for producing phthalic anhydride from o-xylene by air oxidation is set forth in FIG. 1, attached hereto.

The process depicted in FIG. 1 is initiated by pumping o-xylene from storage tank 100 via pump 102 through filter 104 and o-xylene preheater 106, where it is heated almost to the vaporization point. Air is passed through air filter 108, silencers 110 and 114, compressed in air compressor 112, and heated in air preheater 116 before being mixed with the hot liquid o-xylene. The hot liquid o-xylene is injected into the hot air stream via spray nozzles (not shown) and vaporized. The vaporized air-xylene mixture passes through knock-out drums 118. The treated air-xylene mixture then enters fixed-bed reactors 124 and 126. Reactors 124 and 126 each contain vertical tubes packed with various catalysts. The heat of reaction is removed by molten salt circulating in the reactor shell via salt bath cooler and agitator systems 128 and 130, respectively. The salt is cooled by steam coils 132 and 134, which produce steam to be used throughout other parts of the process.

The reaction gas is composed of nitrogen, oxygen, water, carbon dioxide, carbon monoxide, argon, phthalic anhydride, maleic anhydride, maleic acid, o-toluic acid, and partial oxidation products, for example, phthalide, etc.

The reaction gases from reactors 124 and 126 enter gas cooler 136 and secondary gas cooler 138 before being conveyed to switch condensers 140. There are typically a minimum of three switch condensers 140, i.e., two of the switch condensers are on a loading (cooling) cycle and one is on a melting (heating) cycle. The crude phthalic anhydride desublimates onto tubes 141 of the switch condenser, and the remaining gas mixture exits from the switch condenser. The off-gas is conveyed to thermal oxidizers 142 and 144 for incineration.

Switch condensers 140 are cooled by passing low viscosity oil through tubes 141. The cold oil is cooled in a cold oil system by cooling water. In cooler climates, air cooling can be used.

During the heating cycle, hot oil is circulated through tubes 141 of switch condenser 140 to melt the crude phthalic anhydride plated thereon. The liquid anhydride flows into crude product surge vessels 146. The liquid anhydride is thereafter pumped via pump 148 to storage tank 150.

The crude phthalic anhydride liquid is delivered via pump 152, filter 154 and pump 156 to preheater 158 where it is heated to approximately 500° F. The heated crude phthalic anhydride is conveyed continuously through decomposers 160 and 162. The residence time in each decomposer is about 6-12 hours. Decomposers 160 and 162 operate under a slight vacuum (about 700 mm Hg absolute) and high temperatures (e.g., 500° F.) to convert the small amount of phthalic acid that is present to phthalic anhydride. Also, most of the maleic anhydride in the crude is removed by evaporation or chemical reaction. Evaporated impurities especially water are removed via condenser 164 and ejector jets 165. Condensed phthalic anhydride is returned to the decomposers from condenser 164.

Purified phthalic anhydride is pumped from the decomposers via pump 166 to light ends column or fractionation column 168. Column 168 includes reflux condenser 170 and ejector jets (not shown). Low-boiling by-products, e.g., maleic anhydride and benzoic acid, along with a small amount of phthalic anhydride are removed at the top of column 168. Low pressure steam is generated in reflux condenser 170. Crude phthalic anhydride from the bottom of column 168 is fed via pump 172 to either reboiler 174 where it is returned to column 168 or second fractionation column 176.

Pure phthalic anhydride is removed from the top of column 176. Along with the tailings, phthalic anhydride is continuously removed from the bottom of column 176 and sent to reboiler 178 via pump 179 in order to maintain the temperature of the column. Column 176 includes a reflux condenser 180 and ejector jets (not shown). The pure phthalic anhydride from the top of column 176 is sent to phthalic anhydride run-down tanks 182 via pump 184, and eventually stored in storage tanks (not shown).

Various conventional methods for removing water and concentrating phthalic anhydride are set forth in U.S. Pat. No. 3,725,211 (Gehrken et al.), which issued Mar. 1, 1972, U.S. Pat. No. 3,655,521 (Gehrken et al.), which issued Apr. 11, 1972, U.S. Pat. No. 3,507,886 (Suter et al.), which issued Apr. 21, 1970, U.S. Pat. No. 3,397,121 (Fitzgerald), which issued Aug. 13, 1968, U.S. Pat. No. 3,178,452 (Smith et al.), which issued Apr. 13, 1965, U.S. Pat. No. 3,650,906 (Gehrken et al.), which issued Mar. 21, 1972, and U.S. Pat. No. 3,303,203 (Melnstein), which issued Feb. 7, 1967.

Based on recently obtained equilibrium data on the decomposition of the acid together with computer modeling studies, the present inventors have discovered that there can be very little water loss from the system without large losses of phthalic anhydride. Lowering the temperature favors the formation of phthalic acid so the water content of the vapor is depleted by both acid formation and the higher solubility of water in the liquid at the lower temperature. Moreover, the lower temperature frequently leads to plugging the condenser with phthalic acid which has been a major problem in plant operations, often leading to bypassing of the condenser for periods of time, during which losses of phthalic anhydride increase significantly.

The present inventors have discovered that by taking the vapors directly from the decomposer and putting them into the upper tray section of the downstream light ends fractionation column, (preferably just below the column overhead condenser), the decomposer reflux condenser and vacuum system can be eliminated. Moreover, in the fractionation column the water is fractionated away from the phthalic anhydride so that the losses of phthalic anhydride are reduced.

Currently, in order to keep the losses of phthalic anhydride low from the decomposer's reflux condenser, phthalic acid concentration to the column feed would have to increase. This would then increase the water concentration in the overhead section of the column to the same levels as in the present invention. In effect, the method described hereafter by the present inventors allows the water to bypass all but the top section of the fractionation column. The surprising result of eliminating the decomposer condenser and jet ejectors of the decomposer section is that the phthalic acid levels in the decomposer and in the feed to the column are reduced. This in turn reduces the losses of phthalic anhydride and improves product quality by decreasing the level of phthalic acid in the final product.

The present invention also provides many additional advantages which shall become apparent as described below.

SUMMARY OF THE INVENTION

A process for the production of substantially pure phthalic anhydride from crude phthalic anhydride which comprises the steps of: heating crude phthalic anhydride liquid to a temperature below the boiling point of phthalic anhydride; pumping the heated crude phthalic anhydride liquid to at least one decomposer vessel which is capable of decomposing the crude phthalic anhydride liquid; venting decomposer vapor from the decomposer vessel directly to a top portion of a first fractionation column such that phthalic anhydride is recovered from the decomposer vapor; withdrawing phthalic anhydride liquid from the decomposer vessel, optionally cooling the phthalic anhydride liquid, and pumping the phthalic anhydride liquid to the first fractionation column for the separation of residual water and light ends therefrom; withdrawing phthalic anhydride liquid from the first fractionation column and pumping it into a second fractionation column for the separation of tailings therefrom; and withdrawing substantially pure phthalic anhydride from the second fractionation column.

It is also an object of the present invention wherein the decomposer vapor is vented to the top portion of the first fractionation column via a heated conduit. Moreover, the decomposer vapor enters the first fractionation column above the upper trays or packing and below the reflux condenser thereof.

Another object of the present invention is a system for producing substantially pure phthalic anhydride from crude phthalic anhydride which comprises: a means for decomposing the crude phthalic anhydride liquid such that water, various other by-products and small amounts of phthalic anhydride are removed from crude phthalic anhydride liquid as decomposer vapor; a means for venting the decomposer vapor directly to a top portion of a first fractionation column; a first fractionation column which is capable of distilling crude phthalic anhydride liquid received from the decomposer means, i.e., a vessel or tank, to remove light ends therefrom and which is also capable of recovering phthalic anhydride contained within the decomposer vapor and vapor produced during the distillation of the crude phthalic anhydride liquid; and a second fractionation column capable of distilling the crude phthalic anhydride liquid from the first fractionation column and removing tailings therefrom to produce substantially pure phthalic anhydride.

Other and further objectives, advantages and features of the present invention will be understood by reference to the following specification in conjunction with the annexed drawings, wherein like parts have been given like numbers.

DESCRIPTION OF THE PREFERRED EMBODIMENT

Phthalic anhydride is preferably manufactured by catalytic air oxidation of o-xylene, naphthalene and/or any other suitable starting material. The present invention is specifically directed to modification of the finishing section of the process, whereby decomposer vapors are sent directly to the top portion of the light ends fractionation column.

Figure 1:
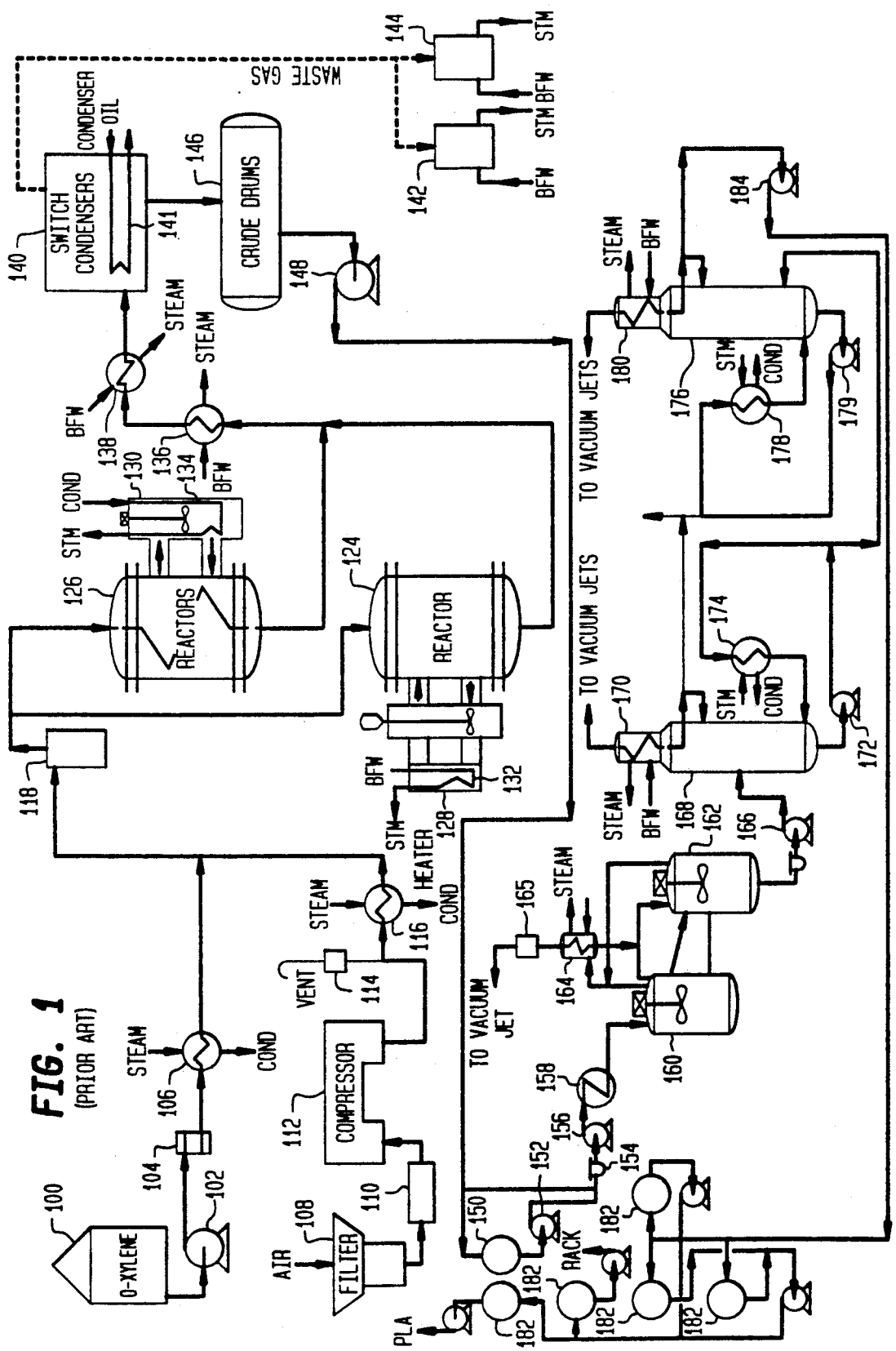
FIG. 1 is a schematic flow chart depicting a conventional fixed-bed vapor-phase system for the oxidation of phthalic anhydride from o-xylene.
Figure 2:
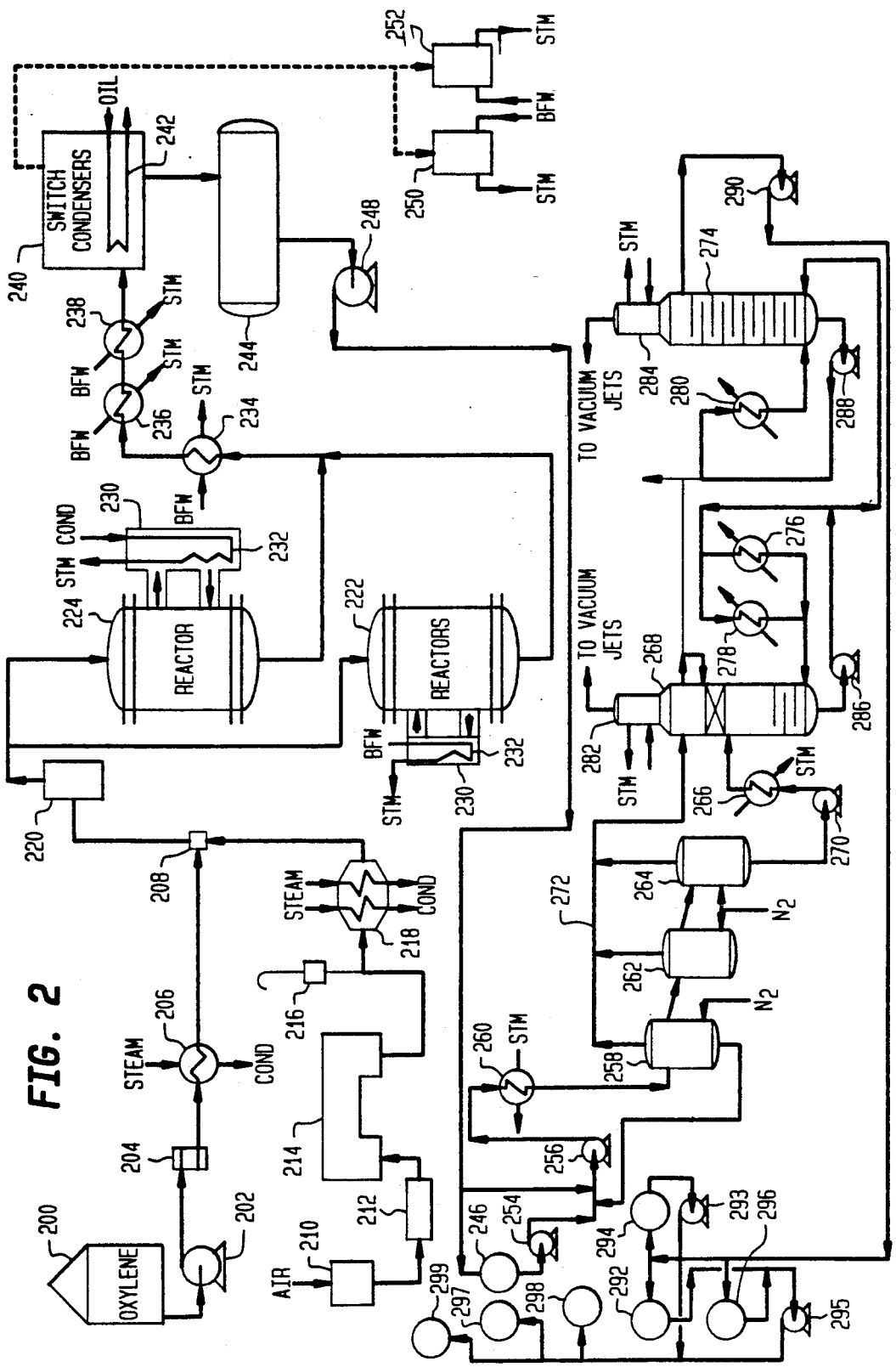
FIG. 2 is a schematic flow chart depicting the vapor-phase system for the oxidation of phthalic anhydride from o-xylene according to the present invention.

The present invention can best be described by referring to the drawings, wherein FIG. 2 is a basic flow chart of the vapor-phase oxidation system used herein. Not only will the system according to the present invention assist in the treatment of decomposer vapors and increase the percent recovery of phthalic anhydride, but it will also increase the overall yearly phthalic anhydride capacity of the system by up to approximately 0.5%.

Orthoxylene is pumped from storage tanks 200 via feed pumps 202 through filters 204 and preheater 206 to air-orthoxylene vaporizer nozzles 208. Preheater 206 is heated by steam. The air supply system consists of air filter 210, silencer 212, air compressor 214, silencer 216, and air heater 218. Air heater 218 uses steam to heat the compressed air and is a two step air heater. That is, air heater 218 includes a preheating stage and final heating stage.

Hot air supplied from the air supply system vaporizes the o-xylene feed at spray nozzles 208 disposed upstream of knock-out pots 220. It is important that all the o-xylene be vaporized in order to prevent liquid o-xylene from reaching the catalyst and causing an ignition thereof.

Individual knock-out pots 220 are upstream of packed tube reactors 222-A/B and 224. Packed tube reactors 222-A/B and 224 each contain thousands of vertical tubes. The heat of reaction is removed by molten salt circulating in the shell. The molten salt is provided to each reactor shell via molten salt circulation systems 230. The salt, in turn, is cooled by steam coils 232.

The heat of reaction in the reactor is removed as steam by means of molten salt circulation systems 230 and the resultant steam can be used elsewhere in the system. The orthoxylene/air vapor sent from knock-out pots 220 to reactors 222-A/B and 224 pass through tubes contained within the reactors. The tubes are packed with a catalyst capable of assisting in the conversion of orthoxylene to phthalic anhydride and various other by-products. One such catalyst is vandium oxide combined with titanium dioxide and coated on an inert, nonporous carrier.

Reactor effluent gas is cooled by passing the effluent gas through a gas cooler 234 attached to each reactor. The effluent gas is then passed through secondary gas coolers 236 and 238 which lower the gas temperature to several degrees below the flammable limit, before entering switch condensers 240.

Switch condensers 240 desublime the effluent gas using the cold condenser oil, and then melt off the crude phthalic anhydride product using the same condenser oil heated with steam. Both the hot condenser oil and cold condenser oil are pumped through switch condensers 240 via tube 242. A substantial amount of impurities exit switch condensers 240 as part of the vapor stream, whereas the crude phthalic anhydride is plated about tubes 242 during the cooling step and exits switch condensers 240 at the bottom during the melt off. The crude phthalic anhydride liquid is sent from switch condensers 240 to surge vessels 244 before being pumped to storage tank 246 via pump 248.

The vapor gas from switch condensers 240 are sent to waste gas incinerators 250 and 252 where it is burned in combination with fuel gas to produce steam. Crude phthalic anhydride is stored in tank 246 disposed upstream of the finishing section. Tank 246 is heated with steam to maintain the crude phthalic anhydride in a molten state.

The key to the present invention resides in the changes to the finishing section of this system. Crude phthalic anhydride from surge vessels 244 is pumped by pump 248 to storage tank 246 or pump 256. The crude product is then sent via pump 254 to pump 256. Pump 256 sends the crude product plus a recycle stream from decomposer vessel 258 through preheater 260, whose outlet sets the initial decomposer temperature. Preheater 260 utilizes steam to heat the crude product.

Figure 3:
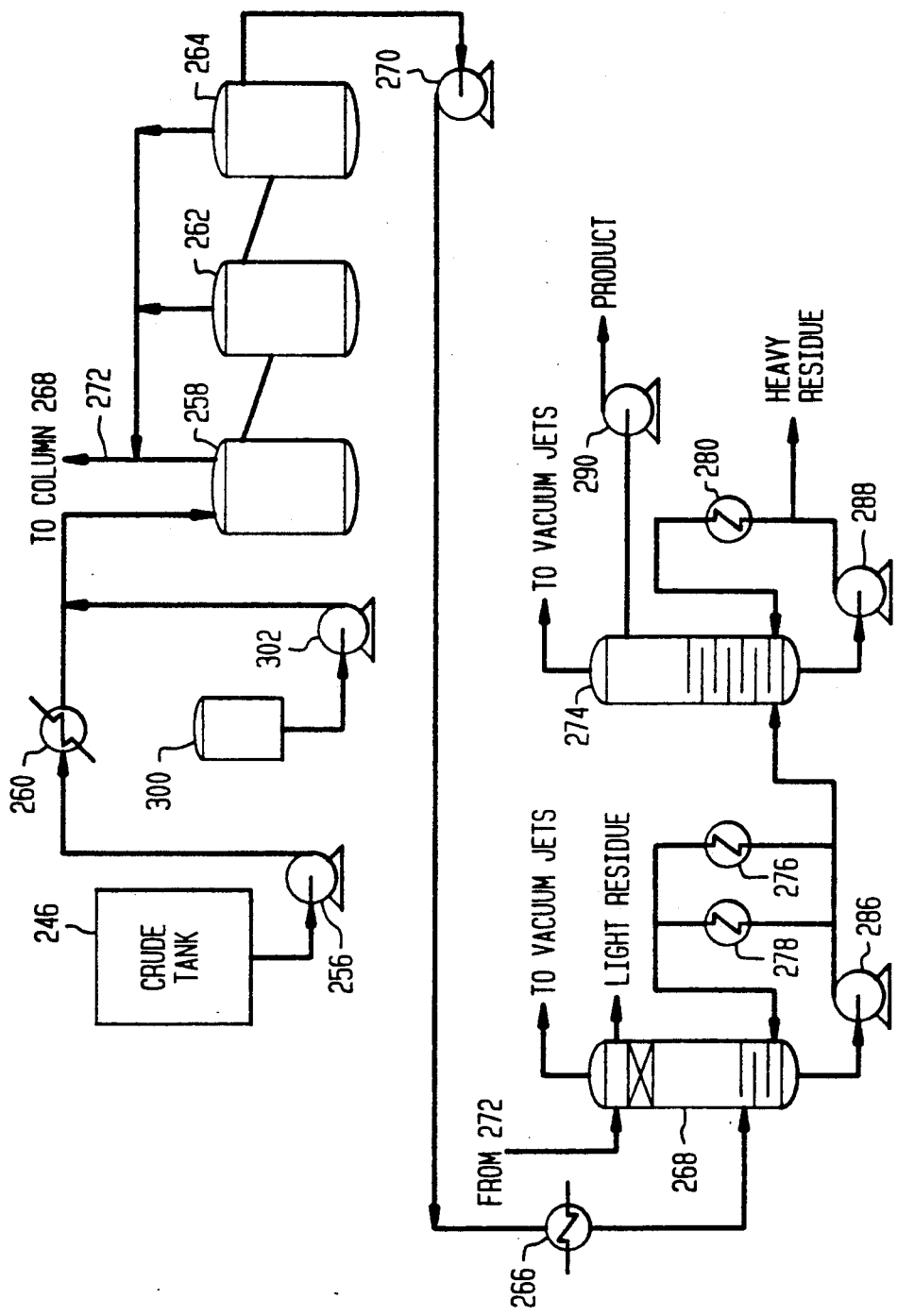
FIG. 3 is a schematic flow chart depicting the finishing section according to the present invention.

As shown in FIG. 3, $Na_2CO_3$ can optionally be added to the system in order to treat the crude phthalic anhydride. $Na_2CO_3$ has a beneficial effect on product quality. A solution of $Na_2CO_3$ in water can be prepared in drum 300 and meter-pumped into decomposer 258.

Crude phthalic anhydride heated in preheater 260 enters decomposer vessel 258 and cascades by gravity through decomposer vessel 262 and decomposer vessel 264. It is then pumped through cooler 266 to light ends fractionation column 268 via pump 270.

Decomposer vessel 258 is heated by external steam panels primarily for start-up. It is agitated to a limited extent by pump 256. Decomposer vessel 258 may be protected against high pressure by a rupture disc (not shown) to incinerators 250 and 252, as are decomposer vessels 262 and 264. The vapor generated from decomposer vessels 258, 262 and 264 is piped via steam-traced conduit 272 directly to the top portion of light ends fractionation column 268.

Elimination of the decomposer condenser and related jet ejectors for treatment of decomposer vapor avoids clogging of the phthalic anhydride return conduit with phthalic acid, reduces the capital equipment cost of the finishing section, and increases the recovery of phthalic anhydride from decomposer vapor. The conventional decomposer overhead circuit, i.e., decomposer condenser and jet ejectors, has historically been a source of operating difficulty, with frequent plugging. Sending decomposer vapors directly to column 268 eliminates this problem and allows the overhead circuit of column 268 to efficiently recover the phthalic anhydride while rejecting water and light ends.

Tables 1, 2 and 3 below show the results of a computer modeling comparison of the conventional finishing section wherein decomposer vapor is sent to a decomposer condenser and jet ejectors and the finishing section according to the present invention wherein decomposer vapor is sent directly to light ends fractionation column 268.

TABLE 1

(DECOMPOSER SECTION)

| | Decomposer Condenser as Reactor at Equil. | Decomposer Condenser as Condenser(5) | Decomposer Condenser Completely Bypassed |
|---|---|---|---|
| Decomp. Temp. | 491° F. | 491° F. | 491° F. |
| Condenser Outlet Temp. | 400° F.(8) | 400° F. | 491° F. |
| RATES, LB/HR(3) | | | |
| Water to Decomp. lb/hr(7) | 7 | 7 | 7 |
| Phthalic Acid to Col. 268(1) | 257 | 209 | 211 |
| Total Vapor From Decomposers | 265 | 143 | 153 |
| Total Vapor Losses From Condenser: | 16.2 | 34.2 | 153 |
| Water(4) | 5.9 | 12.0 | 12.9 |
| PAN(4) | 4.7 | 17.7 | 134.6 |
| Mal. Anh.(2) | 0.4 | 0.4 | 0.7 |
| Inert Gas(6) | 5.2 | 4.1 | 4.8 |
| Total | 16.2 | 34.2 | 153.0 |

Notes:
(1)Based on 337 lb/hr in feed (1 mol %).
(2)Based on 28 lb/hr in feed.
(3)At 30,107 lb/hr crude feed.
(4)Includes water and PAN in the form of phthalic acid.
(5)Assumes no phthalic acid reaction in condenser.
(6)Includes contribution of 2.8 lb/hr N$_2$ instrument purge.
(7)Conservative (high) estimate of free water in crude from, e.g., carbonate addition.
(8)A lower condenser outlet temperature reduces PAN loss, but also rejects less water and hence sends more phthalic acid to column 268. Cases run without the 7 lb/hr free water to the decomposers gave the following results in Table 2 below:

TABLE 2

(DECOMPOSER SECTION)

| | Condenser Outlet at 350° F. | Condenser Outlet at 400° F. | Condenser Outlet at 450° F. |
|---|---|---|---|
| Phthalic Acid to Col. 268 lb/hr | 230 | 220 | 210 |
| Vapor loss from condenser, lb/hr | | | |
| Water | 2.1 | 3.4 | 4.7 |
| PAN | 0.8 | 3.4 | 11.2 |
| Other | 4.4 | 4.3 | 5.3 |
| Total | 7.3 | 11.1 | 21.2 |

TABLE 3

(FINISHING SECTION)

| | OPERATE CONDEN. AT 400° F.(4) | VENT VAPOR DIRECTLY (BYPASS COND.) | SEND VAPOR TO COL. 268 TOP STAGE |
|---|---|---|---|
| KEY RATES, LB/HR(1) | | | |
| To Col. 268 from Decomp. overhead | — | — | 153 |
| To vacuum Jets From PreDecomp. | 34 | 153 | 0 |
| To Vacuum jets from Col. 268 | 142 | 142 | 160 |
| Total to Vac. Jets | 176 | 295 | 160 |
| PERFORMANCE PARAMETERS | | | |
| Phthalic Acid to Col. 268, lb/hr(2) | 209 | 211 | 211 |
| Col. 268 Reflux Ratio on Feed(3) | 0.357 | 0.359 | 0.351 |
| Benzoic Acid Rejection in Col. 268(5), % | 84.1 | 84.3 | 83.6 |
| Col. 268 Top Stage Temperature | 326° F. | 326° F. | 314° F. |
| Total PAN Losses to Vacuum Jets lb/hr | 59.3 | 176.2 | 42.0 |
| Delta PAN Losses, lb/hr | Base | +116.9 | −17.3 |

NOTES:
(1)Based on 30,107 lb/hr crude feed to the Decomposers.
(2)Based on assumption of 337 lb/hr phthalic acid and 7 lb/hr water to decomposers, 491° F. decomposer temperature.
(3)Corresponds to 2.14M Btu/hr reboiler duty for Col. 268.
(4)Arbitrary outlet temperature. A lower temperature reduces PAN loss, but also rejects less water and hence sends more phthalic acid to Col. 268 as shown in Table 2 above.
(5)Based on 47 lb/hr benzoic acid in feed, wherein percent benzoic acid rejection is a measure of column separation effectiveness.

It is readily apparent from review of the above tables that total phthalic anhydride loss to vacuum jets is substantially reduced when the decomposer vapor is sent to the top stage of fractionation column 268 versus sending it either to the decomposer condenser or bypassing the decomposer condenser altogether. This is completely unexpected especially when it is possible to efficiently operate the finishing section without costly decomposer condensers and associated jet ejectors, and at the same time substantially increase the amount of phthalic anhydride recovered from the decomposer vapor.

Tying the decomposer vapor conduits directly into fractionation column 268, however, does create new concerns regarding overpressuring or underpressuring of the decomposer vessels. Overpressure could result from pressure build-up on column 268 up to its safety valve release pressure of 45 psig. Underpressure below the design of 660 mm Hg absolute could be produced by the large fractionation column jet ejector system. The overpressure concern is met by re-specifying the column 268 safety valve release to a pressure compatible with the existing decomposer pressure. A combination of pressure control, nitrogen pressurization control and a vacuum breaker rupture disc on the outlet is provided to prevent a vacuum being drawn below the 660 mm Hg absolute limit for decomposer vessels 262 and 264. Decomposer vessel 258 has been designed for full vacuum and 45 psig consistent with fractionation column 268.

Vapor flow from the decomposer vessels via conduit 272 is under pressure control. Nitrogen pressure control maintains the decomposer vessels at just above atmospheric pressure. Subatmospheric operation is avoided to prevent air leakage into the decomposer vessels.

The fractionation segment of the finishing section consists of first (topping or light ends) fractionation column 268 and second (tailing or product) fractionation column 274, with their respective reboilers, i.e., column 268 is connected to reboiler 276 and spare reboiler 278, and column 274 is connected to reboiler 280. Each fractionation column 268 and 274 includes a reflux condenser 282 and 284, respectively, disposed at the top thereof. Fully spared steam jet ejectors (not shown) are also provided on the top of fractionation columns 268 and 274 to provide column vacuum.

The reboilers are suppressed-vaporization pump-through types with pumps 286 and 288, respectively, which also pump out the bottom products from the associated fractionation column. Finished product from second fractionation column 284 is pumped via pump 290 to product tankage 292, 294, 296, 297, 298, and 299. Pumping the end product to tankage is assisted by pumps 293 and 295.

A projected set of compositions for a future operation in the finishing section is set forth in Table 4 below.

TABLE 4

(Compositions in Finishing Section)

| COMPONENT MOLE % | CRUDE PRODUCT FEED | DECOMPOSER VAPOR | COLUMN 268 VENT VAPOR |
|---|---|---|---|
| H2O | 0.0377 | 30.5404 | 57.4554 |
| N2 | 0.2092 | 13.8583 | 13.0406 |
| O2 | 0.0281 | 1.7478 | 1.3935 |
| CO | 0.0020 | 0.1119 | 0.0984 |
| CO2 | 0.0050 | 0.3208 | 0.2504 |
| MALEIC ANHY. | 0.2759 | 0.7528 | 13.2421 |
| BENZOIC ACID | 0.1237 | 0.2806 | 5.4905 |
| PHTHALIC ANHY. | 97.9447 | 52.3047 | 9.0270 |
| PHTHALIDE | 0.0496 | 0.0233 | 0.0022 |
| TRIMELLITIC | 0.3389 | 0.0117 | 0 |
| PHTHALIC ACID | 0.9890 | 0.0477 | — |

It is readily apparent upon review of Table 4 that the mole percent of phthalic anhydride contained in the vapor vented from the first fractionation column is greatly reduced when compared to the concentration of phthalic anhydride in the decomposer vapor, i.e., 9.0270 mole % (74.74 lb/hr) at 40,615.28 lb/hr of decomposer feed versus 52.3047 mole % (267.92 lb/hr). This indicates a phthalic anhydride recovery from the decomposer vapor of approximately 72.1% when the vapor is vented directly to the fractionation column. Also the amount of water, maleic anhydride and benzoic acid vented is greatly increased by sending the decomposer vapor directly to the fractionation column. As such, the method and system according to the present invention greatly enhances the purification and product recovery of phthalic anhydride.

While we have shown and described several embodiments in accordance with our invention, it is to be clearly understood that the same are susceptible to numerous changes apparent to one skilled in the art. Therefore, we do not wish to be limited to the details shown and described but intend to show all changes and modifications which come within the scope of the appended claims.

What is claimed is:

1. A process for the production of substantially pure phthalic anhydride from crude phthalic anhydride which comprises the steps of:
   heating crude phthalic anhydride liquid to a temperature below the boiling point of phthalic anhydride;
   pumping the heated crude phthalic anhydride liquid to at least one decomposer vessel which is capable of decomposing said crude phthalic anhydride liquid;
   venting decomposer vapor from said decomposer vessel directly to a top portion of a first fractionation column such that phthalic anhydride is recovered from said decomposer vapor;
   withdrawing phthalic anhydride liquid from said decomposer vessel, cooling said phthalic anhydride liquid, and pumping said phthalic anhydride liquid to said first fractionation column for the separation of residual water and light ends therefrom; and
   withdrawing phthalic anhydride liquid from said first fractionation column and pumping it into a second fractionation column for the separation of tailings therefrom and production of a substantially pure phthalic anhydride.

2. The process according to claim 1, wherein said decomposer vapor is vented to said top portion of said first fractionation column via a heated conduit.

3. The process according to claim 1, wherein said first fractionation column includes a reflux condenser at the top thereof wherein phthalic anhydride contained within the vapors from said decomposer vessel and said first fractionation column are condensed and returned to lower sections of said first fractionation column.

4. The process according to claim 3, wherein said decomposer vapor enters said first fractionation column above the upper trays or packing and below said reflux condenser of said first fractionation column.

5. The process according to claim 1, wherein at least two decomposer vessels are connected in series such that crude phthalic anhydride flows by gravity from one decomposer vessel to the next until it is pumped from the last decomposer vessel to said first fractionation column.

6. In a process for the continuous purification of crude phthalic anhydride produced from vapor phase oxidation of o-xylene and/or naphthalene, said process comprising an oxidation section and a finishing section, the improvement comprising a finishing section comprising:
   continuously heating crude phthalic anhydride liquid to a temperature below the boiling point of phthalic anhydride and pumping the heated crude phthalic anhydride liquid to at least one decomposer vessel for decomposing said crude phthalic anhydride liquid;
   continuously venting decomposer vapor from said decomposer vessel directly to a top portion of a first fractionation column;
   continuously withdrawing phthalic anhydride liquid from said decomposer vessel, and pumping said phthalic anhydride liquid to said first fractionation column for the separation of residual water and light ends therefrom;
   continuously withdrawing phthalic anhydride liquid from said first fractionation column and pumping it into a second fractionation column for the separation of tailings therefrom; and continuously withdrawing substantially pure phthalic anhydride product from said second fractionation column.

7. The process according to claim 6, wherein said decomposer vapor is vented to said top portion of said first fractionation column via a heated conduit.

8. The process according to claim 6, wherein said first fractionation column includes a reflux condenser at the top thereof wherein phthalic anhydride contained within the vapors from said decomposer vessel and said first fractionation column are condensed and returned to lower sections of said first fractionation column.

9. The process according to claim 8, wherein said decomposer vapor enters said first fractionation column above the upper trays or packing and below said reflux condenser of said first fractionation column.

10. The process according to claim 6, wherein at least two decomposer vessels are connected in series such that crude phthalic anhydride flows by gravity from one decomposer vessel to the next until it is pumped from the last decomposer vessel to said first fractionation column.

* * * * *